United States Patent [19]

Sakamoto et al.

[11] Patent Number: 4,720,387

[45] Date of Patent: Jan. 19, 1988

[54] SUSTAINED-RELEASE PREPARATION OF PINACIDIL

[75] Inventors: Teruo Sakamoto; Sadao Kawai, both of Osaka; Kinzaburo Noda, Hyogo; Toyohiko Takeda, Hyogo; Toshihiro Ogura, Hyogo, all of Japan

[73] Assignee: Shionogi & Co., Ltd., Osaka, Japan

[21] Appl. No.: 617,567

[22] Filed: Jun. 5, 1984

[30] Foreign Application Priority Data

Jun. 22, 1983 [JP] Japan .................. 58-113027

[51] Int. Cl.$^4$ .............................. A61K 9/24
[52] U.S. Cl. ...................... 424/472; 514/353
[58] Field of Search .......... 424/20, 21, 35, 472, 424/19; 514/353

[56] References Cited

U.S. PATENT DOCUMENTS

| | | | |
|---|---|---|---|
| 2,809,917 | 10/1957 | Hermelin | 424/21 |
| 2,951,792 | 9/1960 | Swintosky | 424/21 |
| 2,953,497 | 9/1960 | Press | 424/20 |
| 2,996,431 | 8/1961 | Barry | 424/20 |
| 3,044,938 | 7/1962 | Halley | 424/19 |
| 3,115,441 | 12/1963 | Hermelin | 424/35 |
| 3,275,519 | 9/1966 | Glasman | 424/21 |
| 3,634,584 | 1/1972 | Poole | 424/21 |
| 3,906,086 | 9/1975 | Guy et al. | 424/20 |
| 3,922,338 | 11/1975 | Estevenel | 424/21 |
| 4,057,636 | 11/1977 | Petersen | 260/294.9 |
| 4,173,626 | 11/1979 | Dempski et al. | 424/21 |
| 4,353,887 | 10/1982 | Hess et al. | 424/21 |
| 4,409,222 | 10/1983 | Arrigoni-Martelli | 514/353 |
| 4,454,108 | 6/1984 | Iida et al. | 424/21 |
| 4,524,060 | 6/1985 | Mughal et al. | 424/21 |
| 4,600,577 | 7/1986 | Didriksen | 514/353 |

OTHER PUBLICATIONS

Eudragit Acrylic Resins at One Glance, Rohm & Haas.

*Primary Examiner*—Shep K. Rose
*Attorney, Agent, or Firm*—Wenderoth, Lind & Ponack

[57] ABSTRACT

Highly effective and orally administrable sustained-release preparation of an antihypertensive agent, pinacidil (N"-cyano-N-4-pyridyl-N'-1,2,2-trimethylpropyl-guanidine) comprising a rapid-release and a slow-release component at a ratio of about 7:3 to about 1:9 by pinacidil weight.

13 Claims, 16 Drawing Figures

SUSTAINED-RELEASE PREPARATION OF PINACIDIL

BACKGROUND OF THE INVENTION

1. Field of the Invention

The present invention relates to the field of pharmaceutical preparations and provides new retard preparations containing pinacidil (N''-cyano-N-4-pyridyl-N'-1,2,2-trimethylpropylguanidine).

2. Description of the Prior Art

In order to continuously maintain the effect of a certain drug, various methods have been attempted which can be classified into the following two categories:

(a) Single phase structure which slowly releases the active ingredient (i.e. prolonged-release type);

(b) Two phase preparations in which one of the two phases is a rapid-release type and the other a sustained-release type (i.e. sustained-release type).

The present preparations are classified into the (b) type. In order to manufacture a retard preparation from a plain drug, it is necessary to clarify the biological or pharmaceutical characteristics as well as physicochemical properties of the drug. Then, the method applicable to the drug is usually selected from a variety of techniques for pharmaceutical preparations according to the above clarified properties.

N-Keflex®, an antibiotic oral-preparation of sustained-release type, consists of two components, i.e. plain granules (rapid-release one) and enteric granules (delayed-release one). In this preparation, the enteric coating granules prolong the absorption of drug in the intestine to give a long-acting effect to the preparation [described in U.S. Pat. No. 4250166, (Jap. Pat. Pub. No. 55-47611)].

In another case, a long-acting granular preparation of the single phase structure containing theophylline, which is used for treating a pulmonary disease, has been described in Japanese Patent Publication No. 55-153715. The preparation of theophylline is a prolonged-release type which contains theophylline as the active ingredient, a metal salt of higher fatty acid and ethylcellulose in a certain amount, from which the active ingredient is released moderately.

SUMMARY OF THE INVENTION

The present invention relates to new sustained-release preparations containing pinacidil, more particularly, to mixed preparations consisting of a rapid-release component and a slow-release one. The invention provides the long-acting preparations of pinacidil which can be applied safely and conveniently.

Figure 3:
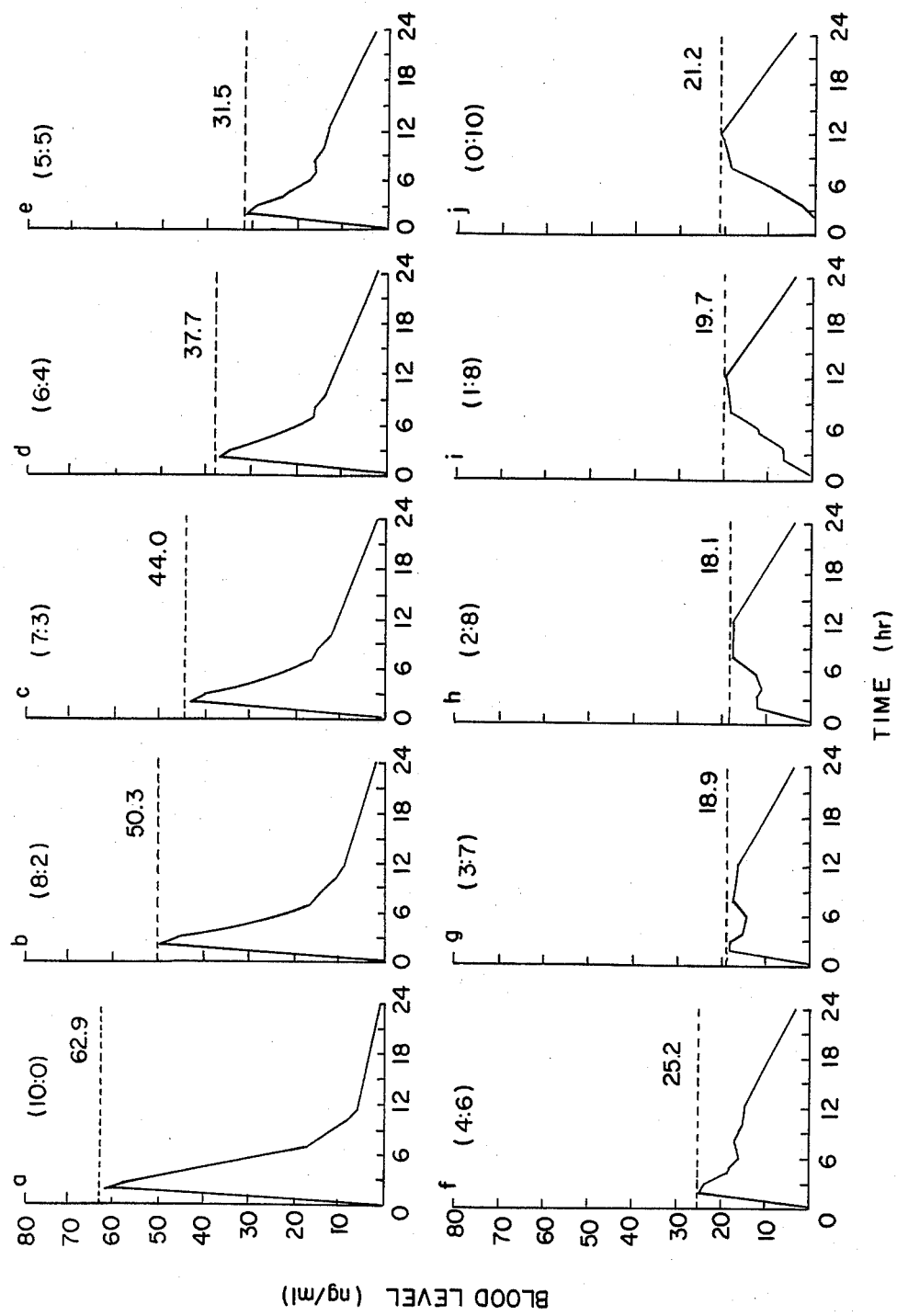

Each graph a-j in FIG. 3 shows the expected blood-level curve and its maximum value on administration of the sustained-release preparations (at a dose of 10 mg as a total amount of pinacidil) having the respective combination-ratio indicated in each graph. In every graph, the ordinate shows the blood-level of pinacidil and the abscissa shows time (hr).

Figure 4:
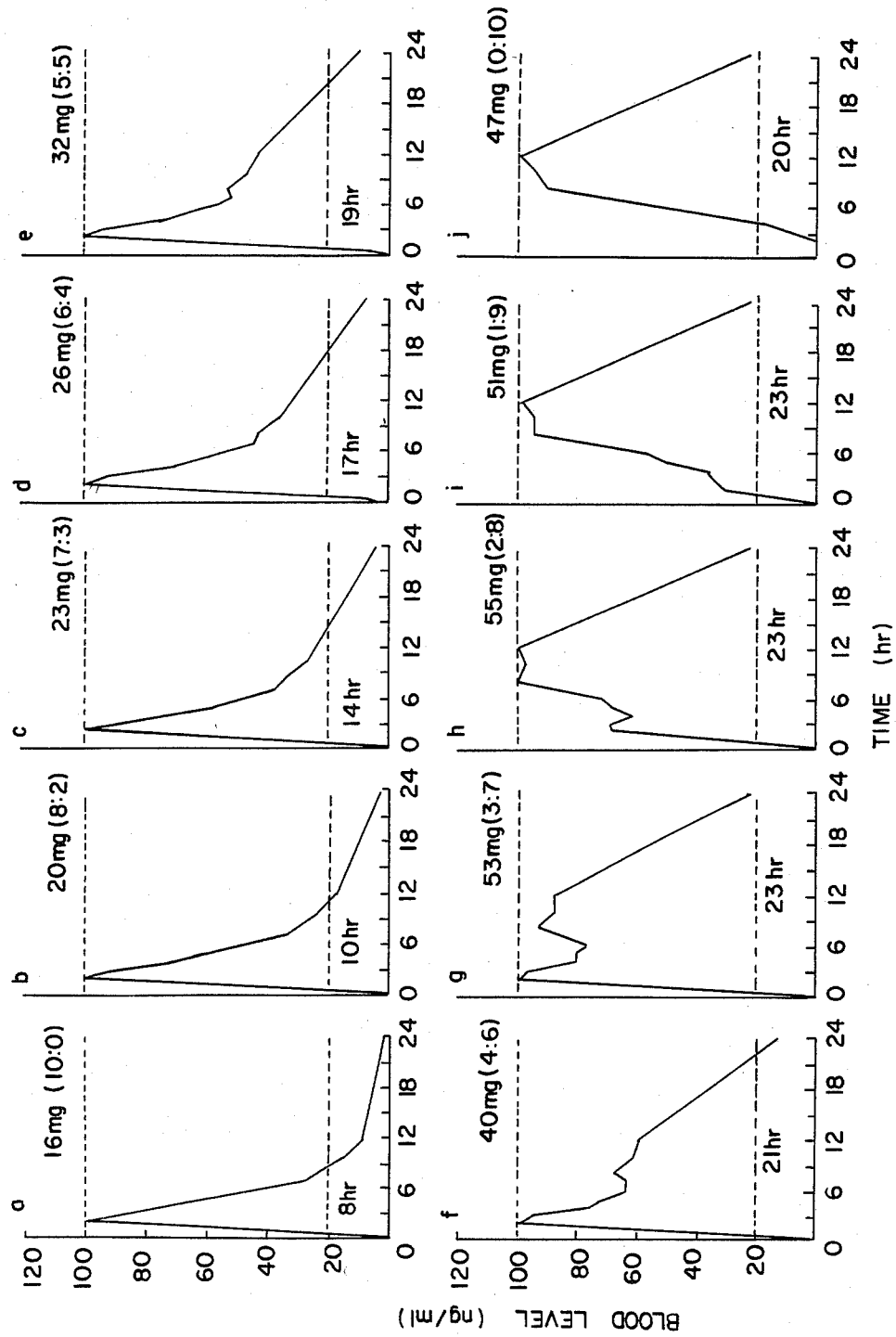

Each graph of a-j in FIG. 4 shows the permissible maximum dose (single dose) of pinacidil at which the maximum blood-level of pinacidil reaches 100 ng/ml in comparison with the corresponding blood-level curve and the period during which the blood-level is maintained over the minimum effective level (20 ng/ml) among the mixing ratio of the respective preparations.

Figure 5:
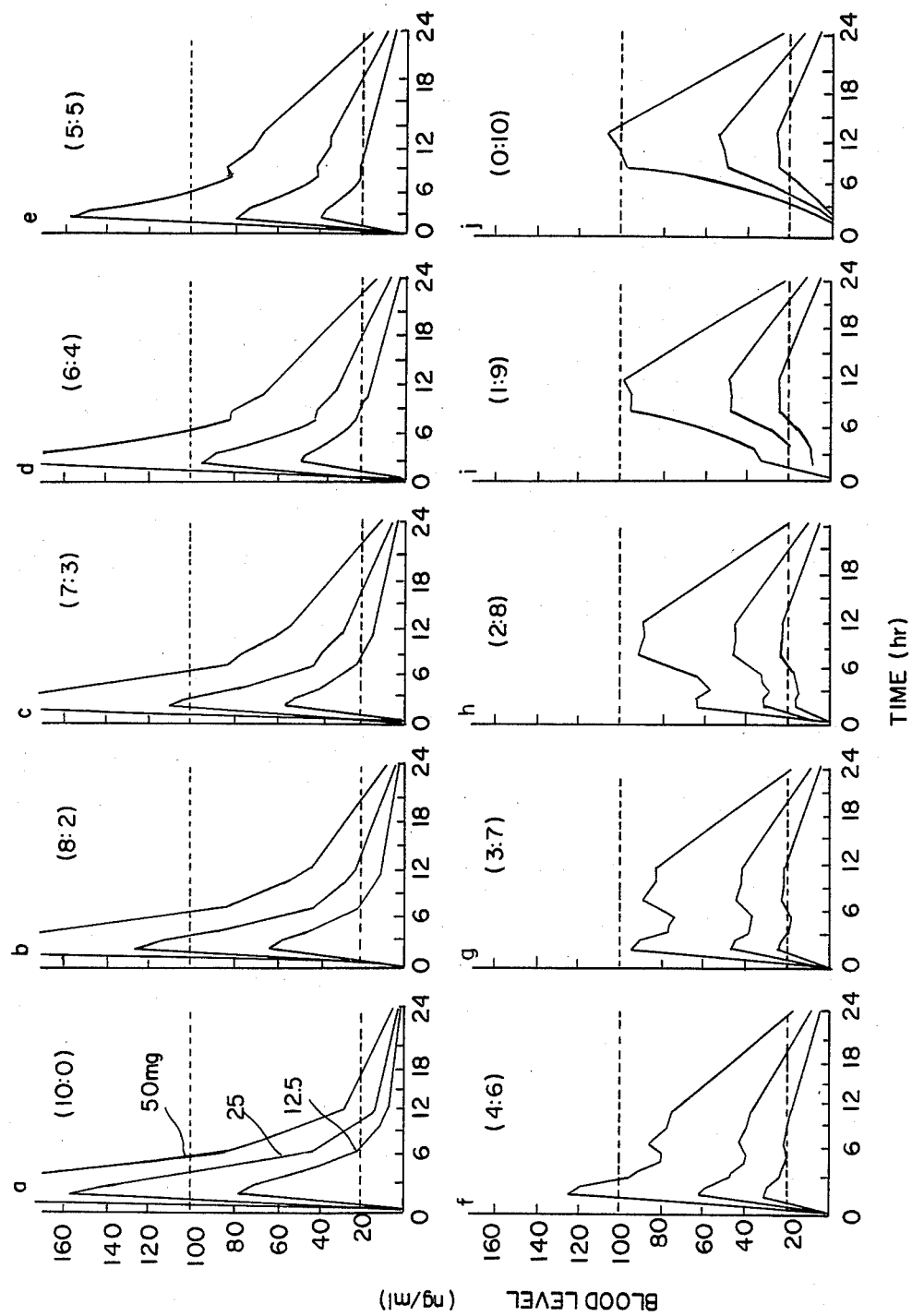

Each graph a-j in FIG. 5 shows the expected blood-level curves at three dosage levels (12.5 mg, 25 mg or 50 mg) with regard to the respective combination ratio. The ordinate shows the blood-level of pinacidil and the abscissa shows time (hr).

Figure 6:
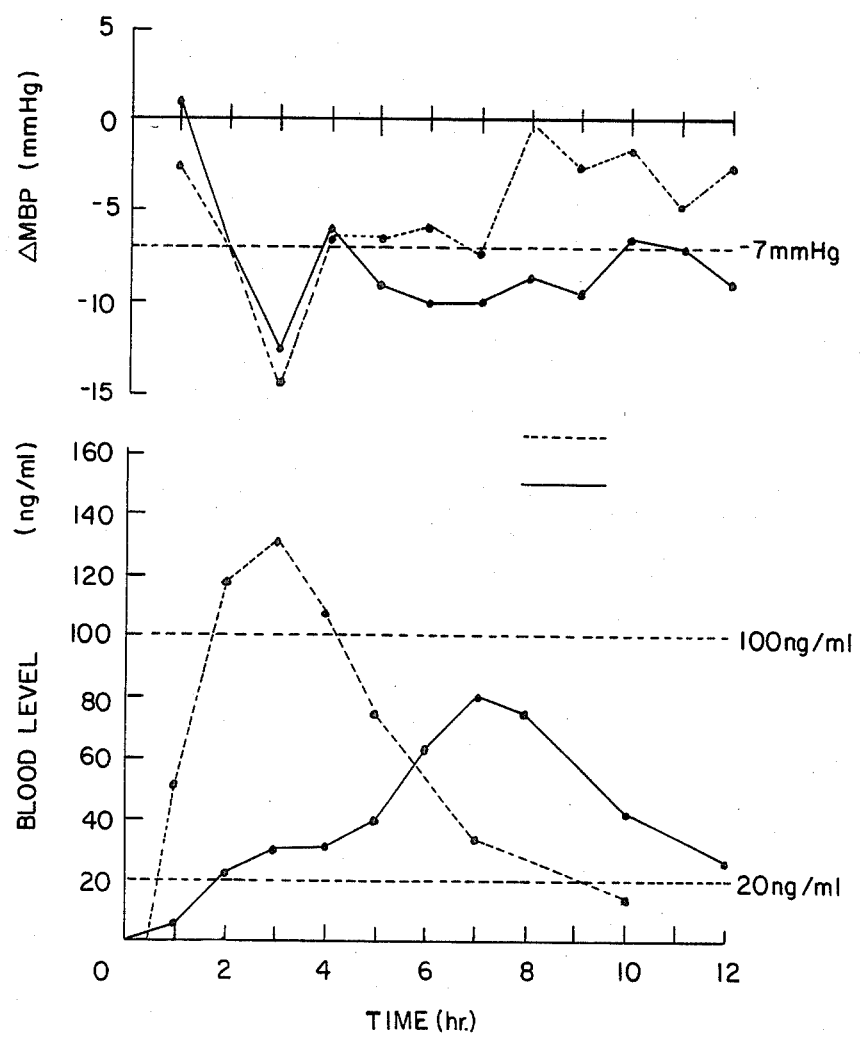

FIG. 6 shows the relationship between the blood-level of pinacidil and the degree of antihypertension (ΔMBP), each of which is an average of the values observed when the rapid-release component or sustained-release component are administered to four healthy volunteers at a dose of 20 mg as pinacidil. In the figure, the curves represented by the dotted line are in case of the rapid-release component and the curves by the full line are of sustained-release preparations. The ordinate shows the blood-level of pinacidil or ΔMBP, and the axis of abscissa shows time.

Figure 7:
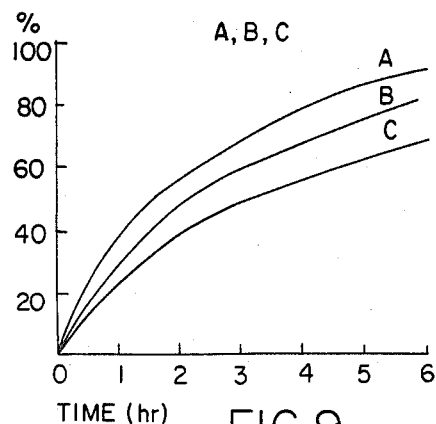
Figure 8:
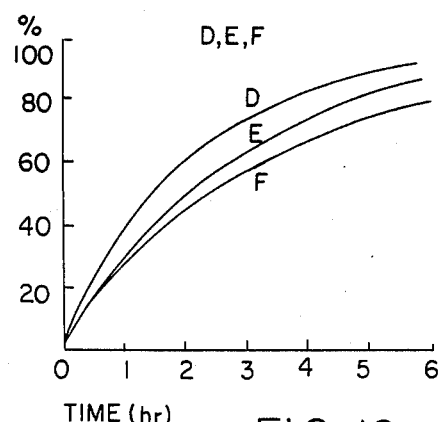
Figure 9:
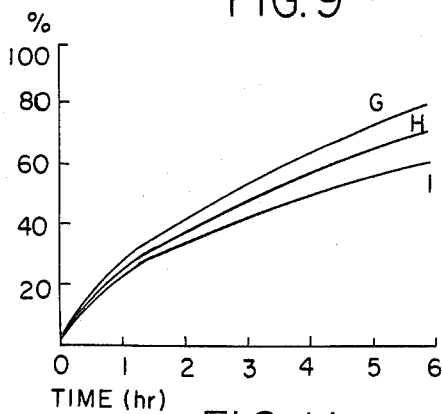

FIGS. 7, 8 and 9 show dissolution curves of the components A, B and C, the components D, E and F and the components G, H and I respectively in the second fluid (J.P. X). The ordinate shows dissolved percent of pinacidil and the abscissa shows time.

Figure 10:
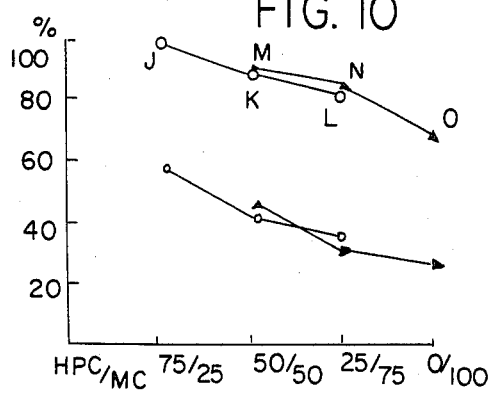

FIG. 10 shows the rate of dissolution of the components J to O in the second fluid one hour after or six hours after the immersion. The upper groups represented by the dots J to O or the lower groups by the dots J to O show the respective dissolution rates six hours after or one hour after the immersion, respectively. The ordinate shows dissolved percent and the abscissa shows the ratio of hydroxypropylcellulose (HPC)/methylcellulose (MC) in the respective components.

Figure 11:
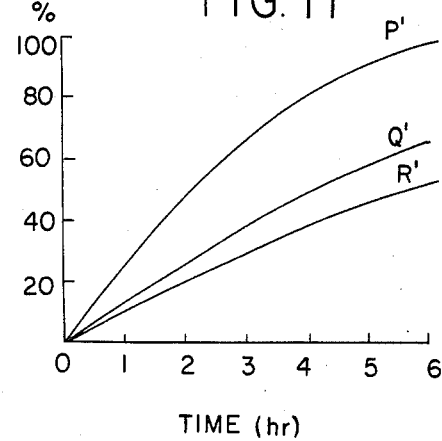

FIG. 11 shows the dissolution curves of the preparations P', Q' and R' in the second fluid. The ordinate shows the dissolved percent and the abscissa shows time (hr).

FIGS. 12, 13, 14 and 15 show the dissolution curves of the respective components B', E', H' and S in the first fluid and in the second fluid (J.P. X). In each figure, the lower curve shows the dissolution curves of the respective components over time in the first fluid, and the upper curve shows that in the second fluid. The ordinate shows the dissolved percent, and the abscissa shows time (hr).

Figure 16:
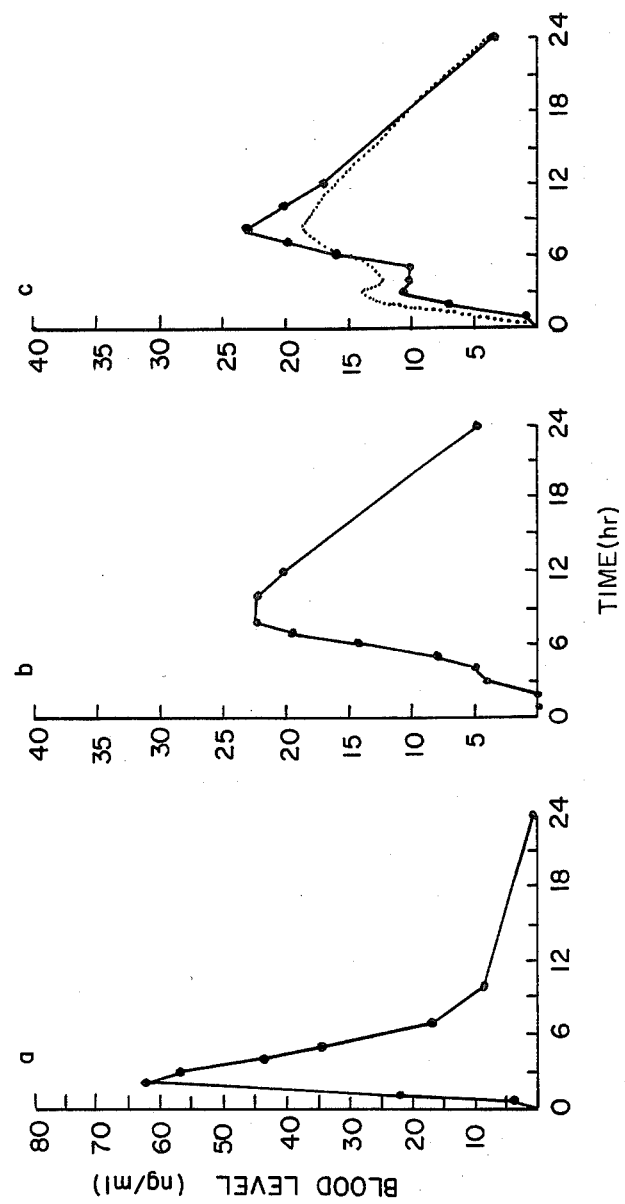

The curves represented by the full line of the graphs a, b and c in FIG. 16 show the blood-level after the administration of the rapid-release granules, the slow-release granules and the multi-layer granules at a dose of 20 mg as pinacidil respectively. Moreover, the curve represented by the dotted line shows the expected blood-level which is estimated from the curves in the figures a and b by the proportional calculation. The ordinate and the abscissa in each graph show the blood-level of pinacidil and time (hr) respectively.

DESCRIPTION OF THE PREFERRED EMBODIMENT

Pinacidil is a new and potent hypotensive drug; however, it is also disadvantageous in that it is excreted so rapidly as to exhibit the hypotensive action and occasionally accompanied by adverse reactions. Then, in the present invention it was attempted to administer pinacidil at a variety of dosages to a few inpatients suffering from hypertension in order to observe what dosage level of pinacidil causes such undesirable side-effects. During the study, it was found that the higher dosage to afford an sufficient therapeutic time has usually induced the adverse reaction (i.e. headache), and it was also assumed that the continuation of hypotensive action and the occurence of adverse reaction are much influenced by the blood-level of pinacidil. In this connection, the inventors determined the minimum blood-level of pinacidil to exhibit the hypotensive action, and the maximum blood-level under which the adverse reactions are avoidable by administering pinacidil to volunteers.

In this experiment, it is necessary to maintain the blood-level of pinacidil in a range of from the minimum effective concentration to the maximum intoxic concentration (hereinafter referred to as therapeutic range) when pinacidil is administered to the inpatients suffering from hypertension. When pinacidil is administered after a meal, the blood-level increases rapidly and reaches the maximum concentration within 1-3 hours after the administration, and is then excreted in a biological half-life period of 1-2 hours. Even at the highest dosage of pinacidil (unprepared) to avoid the adverse reaction, the effective blood-level is kept only for about 6 hours. Therefore, native pinacidil preparations must be administered three or four times a day; it is very troublesome that so frequent and daily administrations are imposed on the patients.

Under such unavoidable conditions requiring long-term and frequent administration, the patients take the drug sometimes irregularly in disregard of the prefixed administration time, for example, failure of administration.

As mentioned above, pinacidil has the excellent activity but on the other hand it has some serious disadvantages, for example, its short acting-time and occurrence of the adverse reaction at high doses. Therefore, it is very hard to dissolve the problem without depending upon new pharmaceutical techniques. The sustained-release preparations of pinacidil prepared by pharmaceutically modifying native pinacidil in the present invention are the first ones to overcome the problem mentioned above.

In order to elucidate the relationship between the adverse reaction and the blood-level of pinacidil, the present inventors have attempted to administer native pinacidil, i.e. not formulated for sustained release, to a few volunteers at a variety of prefixed doses and observed the occurrence of the adverse reaction and the time-dependent change of the blood-levels. In this experiments it was found that an excess dosage giving over 100 ng/ml of the blood-level of pinacidil occassionally causes some side-effects (i.e. a headache). [referred to Exp. 6-II), Table 12].

On the other had, in order to determine the minimum effective blood-level of pinacidil, the relationship between the antihypertensive effect and the blood-level of pinacidil was investigated. As a result, it was found that the antihypertensive effect was minimum at the blood-level around 20 ng/ml but satisfactory at over 30 ng/ml. In view of the above facts, the minimum effective blood-level of pinacidil was tentatively fixed at 20 ng/ml and the maximum safety level at 100 ng/ml. According to this restriction, the inventors intended to make sustained-release preparations of pinacidil which maintain the effective blood-level not exceeding the maximum safety level as long as possible. In other words, the preparations were formulated so that when they are administered at a proper dose, the blood-level of pinacidil is maintained in a range of 20 to 100 ng/ml, preferably 30 to 80 ng/ml for an extended period of time.

It is assumed that the most preferred blood-level profile of pinacidil requires the following conditions;
(1) the blood-level is rapidly increased after the administration;
(2) the effective blood-level is kept for an extended period of time;
(3) in addition to the above items (1) and (2), the efficiency of absorption of pinacidil is retained at a level comparable to that of native pinacidil. The preparations provided with the above three conditions give a desired blood-level profile over a long period of time when a proper amount of them is administered. In preparing the aforementioned preparations, it is presumed that the condition of the item (1) is not satisfied in a simple way for slow-releasing.

In order to satisfy the item (1), the desired preparations need to contain a rapid-release portion (native pinacidil preparations) in addition to the slow-release component which satisfy the item (2). In this invention, the preferred ratio of pinacidil contained in the rapid-release component and the slow-release component was sought and, thus the preparations which satisfy the both items (1) and (2) were produced. In this invention, chemical modification of pinacidil or means of administration combined with excretion-inhibitors such as probenecid have not been employed for retardation; the retardation was achieved by combining the initial dose to the repeat dose at a reasonable ratio.

(A1) Preparation of slow-release component

In order to provide the preparations which satisfy the item (3), various kinds of slow-release component were administered to volunteers at a single dose after breakfast, and the blood-level of pinacidil were assayed by HPLC (High Performance Liquid Chromatography). From these experiments, it has been found that any enteric-coated component of pinacidil formulated into granules, beads, tablets and so on, which contains a hydrophilic additive and/or a release-retarding agent, gives the desired blood-level profile. In this invention, the retarding type component indicates those in which the surface is gradually dissolved in a simulated intestinal fluid (defined as the second fluid for the disintegration test in Pharmacopoeia of Japan), and the non-disintegration type component indicate those which slowly release pinacidil as an active ingredient in the second liquid over a long period of time during which the original shape is retained.

In this invention, the hydrophilic additives include any of pharmaceutically acceptable bases which have hydrophilicity and are per se sparingly soluble in water. Representative of water soluble additives are sugars such as lactose, sucrose, glucose, D-mannitol, sorbitol, inositol, dextrin and xylose. Water insoluble or sparingly soluble additives are cellulose derivatives or minerals such as starch, crystalline cellulose, talc, calcium phosphate, calcium lactate and calcium carbonate. As further additives, the following surfactants are enumerated: sodium laurylsulfate, polysorbate 80, sucrose fatty acid esters, polyoxyethylene, higher aliphatic alcohols and so on.

In case of using the sugar and/or the cellulose derivatives as hydrophilic additives, they may be added in an amount of 40–90% by weight, preferably 60–80% by weight to the total amount of the slow-release component.

On the other hand, as retarding agents any of conventionally used hydrophobic additives may be employed, for example, higher fatty acids (stearic acid, palmitic acid, myristic acid and so on), metal salts of higher fatty acids (magnesium stearate), waxes (carnauba wax, bees wax, paraffin wax), fats and oils (cacao butter), hydrogenates of wax, or fats and oils (hydrogenated castor oil) and so on. These additives may be used alone or in a mixture of two or more additives.

In case of using the metal salts of higher fatty acids and/or hydrogenated fats and oils as the hydrophobic additives, they may be added in an amount of 2–30% by weight, preferably 5–20% by weight to the total amount of the slow-release preparations.

In this invention as mentioned in the experimental part, the sustained-release preparations of pinacidil which have a desired absorption-rate as well as a desired releasing-rate are made by combining pinacidil with the said hydrophilic additives and/or retarding agent at a proper ratio. The preferable choice and combination-rate of these ingredients vary with the employed preparation method and the amount of pinacidil contained in the preparations. Since pinacidil is very sparingly soluble in the intestinal juice in which pinacidil is diffused, compression preparations, for example, granules having a fine internal structure which are manufactured by a wet granulation method show a preferred diffusion-rate on addition of a proper amount of a hydrophilic additive; in some cases it is not necessary to add a retarding agent (Exp. 1.). However, if the content of pinacidil is low, it is appropriate to add a proper amount of retarding agent to control the release-rate, even though the method of preparation is the same as above (Exp. 2.).

For example, in the case that D-mannitol as a hydrophilic additive and magnesium stearate as a retarding agent are employed in manufacturing slow-release granules by means of wet granulation procedure, D-mannitol/magnesium stearate may be used in a ratio of (90%/0%) to (60%/30%), preferably (70%/20%) to (75%/15%) to the total amount of the granules.

On the other hand, the slow-release component which are made by a centrifugal fluidizing granulation method or fluidized-bed coating method is more porous than the granules made by a wet granulation method. Therefore, the diffusion of the component is accelerated, so it is necessary to take into consideration the ratio of (a hydrophilic additive/an retarding agent), the kind thereof and the amount thereof to the total amount of the slow-release component.

In the case where the slow-release beads are made with D-mannitol as a hydrophilic additive and hydrogenated castor oil and/or magnesium stearate as a retarding agent, by a centrifugal fluidizing granulation method, they may be used in a ratio of, for example, (40%/11%)–(32%/16%).

They may be formulated into the desired forms by means of a conventional method; for example, granules may be prepared by formulation of cylindrical granules with a proper amount of suitable binders by a wet granulation method followed by enteric coating. It is appropriate to make the above cylindrical granules round before the drying-step by a marumerizer or a rapid-mixer in order to facilitate enteric coating or capsule filling. On the other hand, the slow-release beads (spherical particles) may be prepared by adding pinacidil and a retarding agent and/or a hydrophilic additive each alone or as a mixture of them into a core substance such as Non-pareil [Freund Inc., Co.], granulation the mixture by centrifugal fluidizing granulation or fluidized-bed coating method to yield sustained-release spherical beads and further coating the latter with an enteric coating layer.

As a binder, a generally used one may be employed. Since the binders to be used have much influence on the release-rate for the active ingredient, it is necessary to choose a suitable binder according to the kind or the amount of the hydrophilic additives and the retarding agents to be employed and to the dosage form of the preparations. For example, the binders are methylcellulose, hydroxypropylcellulose, hydroxypropylmethylcellulose, hydroxyethylcellulose, dextrin, gelatin, starch, polyvinylpyrolidone and so on.

The rapid-release or slow-release component prepared above are coated with an enteric coating base (methyl methacrylate methacrylic acid copolymer, carboxymethylethylcellulose, cellulose acetate phthalate, white shellac, hydroxypropylmethylcellulose phthalate, polyvinylacetate phthalate, ethyl acrylate methacrylic acid copolymer methylacrylate methacrylic acid methylmethacrylate copolymer and the like) to make slow-release component; or it is also possible to control the release-rate of the slow-release portion by addition of a water soluble additive. The releasing-rate of the slow-release portion may be controlled by using water-insoluble coating bases (such as ethylcellulose, ethylacrylate methylmethacrylate copolymer, ethylacrylate methylmethacrylate, trimethylaminoethylmethacrylate chloride copolymer) alone or in a mixture with enteric coating bases (cellulose acetate phthalate, carboxymethylethylcellulose, hydroxypropylmethylcellulose phthalate, methylmethacrylate methacrylic acid copolymer, polyvinyl alcohol phthalate, styrene maleic acid copolymer, white shellac, polyvinylacetate phthalate, vinylacetate crotonic acid copolymer, methylacrylate methacrylic acid methylmethacrylate copolymer, ethylacrylate methacrylic acid copolymer and the like) or water-soluble additive.

(A-2) Preparation of the rapid-release component

In this invention, any formulation which is made without specific retarding agents in particular may be applied to the rapid-release component; for example, in the form of native pinacidil, powder in which pinacidil may be diluted several or several hundred times with a hydrophilic and well-dispersed excipient, fine granules, granules or beads which are conventionally made by adding further hydrophilic binders to the above powder. The resulting rapid-release component may be formulated into capsules or tablets in combination with slow-release component according to the conventional manner. Alternatively, rapid-release component may be coated on the surface of the slow-release component in form of granules, beads or tablets, by a coating method.

(B) Search for the combination ratio

In order to select the appropriate combination-ratio (pinacidil weight in the rapid-release component to that in the slow-release ones) in the sustained-release preparations of pinacidil, the ratio which would give the blood-level profile satisfying the aforementioned items (1) and (2) was sought according to the following steps.

(B-1) The optimum ratio of combination

Non-processed rapid-release preparations and slow-release component made through the retarding process as mentioned above are respectively administered orally to volunteers after breakfast at a dose of 10 mg (as native pinacidil) in a crossover study, and then the blood-level of pinacidil was analyzed. In FIG. 3, the blood-level curve defined as 10:0 or 0:10 shows the average of the blood-levels (actual values) as to the respective two preparations in the above trial. The curve defined as 10:0 shows the change of the average blood-level which is obtained when the rapid-release component alone are administered at a dose of 10 mg (as pinacidil). The curve defined as 0:10 shows that on the administration of pinacidil (10 mg) as the slow-release component containing no rapid-release component. Each area under the curve (AUC) as to the rapid-release component or the slow-release one has nearly the same value, from which it was comfirmed that the said release-prolonging procedures cause no decrease of the absorption efficiency in the body. Respective blood-level curves represented by the ratio of 8:2–1:9 (the rapid-release portion to the slow-release one) were drawn in the relationship between the expected blood-level and the time elapsed, which was obtained by means of proportional calculation based on the blood-level (average of the actual values) at the ratio of 10:0 and 0:10, on the assumption that the preparations consisting of the rapid-release portion and the slow-release one at the respective ratio as aforementioned was administered at a dose of 10 mg as a total amount of pinacidil.

It may be assumed that the most preferable blood-level profile which satisfies the said item (2) is that of the 2:8 preparations in which the maximum concentration shows the lowest value among the respective blood-level curves since the sum of pinacidil content is in the same in the respective preparations.

(B-2) Acceptable range of the combination-ratios

The permissible range of the combination-ratios was determined as follows. In order to determine the maximum content of pinacidil in the rapid-release portion to the total amount of pinacidil, the respective blood-level curves (FIG. 4), each of which showed the maximum concentration of 100 ng/ml, were drawn by means of proportional calculation from the data shown in FIG. 3. Since it is well known that the blood-level of pinacidil increases in proportion to its dose level, it is possible to indicate on each curve the estimated dosage (total amount of pinacidil) required for attaining the maximum blood-level of 100 ng/ml and the estimated time (hrs) during which the blood-level is maintained over 20 ng/ml.

From FIG. 4, it is seen that the blood-level profile wherein the pinacidil concentration is maintained over 20 ng/ml for 12 hours or longer, falls under the effective and safety zone of 20–100 ng/ml blood-level as defined above, from which the combination-ratio of the rapid-release portion to the slow-release one to give such a blood-level profile can be deduced. Clearly from this figure, the maximum content of pinacidil in the rapid-release component accounts for 70% to the total amount of pinacidil by weight, namely the upper limitation of the rapid-release portion is 7 parts to 3 parts of the slow-release portion.

Then, the respective ratios within a range of 7:3 to 0:10 satisfy the aforementioned definition, but the sustained-release preparations of 0:10 cannot give the blood-level profile satisfying the above item (1). Therefore, the preparations of the ratio 0:10 are unsuitable for the purpose of this invention. Moreover, in order to determine the minimum content of pinacidil in the rapid-release component to the total amount of pinacidil, the blood-level curves corresponding to the dosage of 12.5 mg, 25 mg, and 50 mg were drawn in the same way as mentioned above (FIG. 5). From FIG. 5, it is clear that although the blood-level in the 0:10 preparations is maintained over 20 ng/ml at a dose of 25 mg pinacidil for about 14 hours, the resulting pattern does not satisfy the item 1). Accordingly, the preparations of 0:10 do not accord with the purpose of this invention.

This result is supported by the fact that the blood-level profile of the said ratio 0:10 at a dose of 47 mg pinacidil (in FIG. 4 as an estimated dose), which is the maximum dose of the preparations at that ratio, does not satisfy the above item 1).

On the other hand, the preparations with the ratio 1:9 satisfy the above item (1) because the blood-level at a dose of 25 mg is kept at over 20 ng/ml for about 14 hours and moreover, the blood-level at an increased dose of 50 mg is raised rapidly after administration and kept still under the maximum safety blood-level as defined above. From these results, it seems that the combination-ratio in this invention is allowed within a range of about 7:3 to about 1:9, which is defined as the ratio of the rapid-release portion to the slow-release one.

As shown in FIG. 5, it is clear that the blood-level profile of the 2:8 preparations shows the longest effective period of time which results from the comparison of the effective periods (the time during which the maximum effective concentration of pinacidil is maintained over 20 ng/ml) among every blood-level profile at a dose of 25 mg pinacidil (as a total amount of pinacidil). This finding is consistent with the result of determination of the optimum combination-ratio in B-1). Moreover, the fact is further confirmed from FIG. 4 which indicates that the highest dosage (the estimated total amount of pinacidil which can be administered safely in each combination-ratio) is permitted in the preparations of 2:8.

(C) Estimation of the effect

On the basis of these findings, the relationship between the blood-levels and the antihypertensive effect was investigated on the preparations of 2:8 (rapid-release portion: slow-release one) which gave the lowest blood-level among all the subject preparations at the same dose.

FIG. 6 shows the relationship between the blood-level and the corresponding $\Delta$MBP (MBP: Mean Blood Pressure), wherein the data was obtained by administration of the 2:8 preparations at a dose of 20 mg pinacidil to four volunteers. The term $\Delta$MBP means the difference of the changes of the blood pressure between the day of no drug administration and the day of the administration at the same time of the respective days, and in the figure, the each curve is represented by an average of the actual values of the four volunteers. Moreover, the curve drawn as a control in the same figure was obtained in the same way as mentioned above wherein pinacidil preparations (20 mg as pinacidil) to which no prolonged-release operation was applied were administered to the same volunteers.

In general, the criteria for estimation of the effect on antihypertension is that when the $\Delta$MBP value is over 7 mmHg, the subject drug is appraised at "slightly effective". According to the criteria, a line has been drawn at 7 mmHg of $\Delta$MBP in the figure in order to make the estimation with ease. As seen from the figure, the blood-level of pinacidil reaches 20 ng/ml within 2 hours after administration of the sustained-release preparations at which time the occurrence of the efficacy has already been observed. Additionally, the blood-level after 12 hours from administration is maintained over about 30 ng/ml along with the continuous effect.

On the other hand, the rapid-release component affords the maximum blood-level of pinacidil exceeding that for 100 ng/ml, over which the level increases the frequency of the adverse reaction.

In spite of such a high blood-level produced by the rapid-release component, it does not seem that the blood-level is a major factor in efficacy as seen from the relationship between the blood-level and the corresponding efficacy observed after the administration of the sustained-release preparations. It is seen that the effect gradually declines from 4 hours after administration of the rapid-release component further is decreased after 7 hours.

Table 12 shows the actual values of the blood-level of pinacidil, which are based on FIG. 6 (the curves in FIG. 6 are shown by the average values for four volunteers every hour), and the asterisk attached to the blood-level values indicates that the corresponding subjects are suffering from an adverse reaction (mainly headache) at that time. Table 12 shows the relationship between the blood-level and the occurrence of the adverse reaction in which the experiment was carried out in two groups; to one group, the rapid-release preparations were administered and to the other the slow-release preparations were given; the dosage of pinacidil was the same (20 mg) in both groups; the same volunteers were employed in the both experiments. The frequency of the adverse reaction was compared between the two groups. From this table, it is clearly seen that the occurrence of adverse reaction of the group to which the sustained-release preparations have been given is evidently avoided even in the case wherein the experiment is performed with the same subjects at the same dose of pinacidil as in the group to which the rapid-release component have been given.

Finally, it is concluded that in the present invention the pinacidil preparations which exhibit prolonged actions with lesser side-effects at an unaltered dose are prepared by means known in the art for pharmaceutical formulation. Moreover, the action of pinacidil is maintained continuously for a long-period of time without decrease of the efficacy. From these points of view and the principle of drug formulation, with ensuring both the largest effect and the least dosage, the sustained-release preparations of pinacidil in this invention are in accord with the purpose of this invention.

(D) Formulation

The present sustained-release preparations are prepared so that the ratio of pinacidil of the rapid-release portion to that of the slow-release portion is within a range of about 7:3 to about 1:9 by weight. The rapid-release portion means a native pinacidil on which no prolonged-release procedure is applied, rapid-release component or a portion of the sustained-release preparations from which pinacidil is rapidly released at any region of the normal pH-range in the digestive tract. This rapid-release component is well absorbed from the digestive tract because of high solubility of pinacidil as the active ingredient in an acidic medium. The component may be made into any formulation such as powder, fine granules, granules, beads, syrup and so on, as long as they are practically stable under the conditions of conventional preservation.

On the other hand, the slow-release portion means the preparations of pinacidil to which prolonged-release procedure is applied, such as fine granules, granules, beads and the like.

In order to formulate them into sustained-release preparations, the two different type components aforementioned may be combined each other at a ratio within the range as defined above to give mixed granules or mixed beads, which may further be filled in suitable readily soluble hard capsules (hereinafter referred to as capsules) or formulated into tablets in the conventional method. It is also appropriate to make such preparations that the slow-release component is covered with the rapid-release portion; the thus prepared granules or beads may be employed as such or as capsules containing them or tablets made in the conventional manner.

It is noteworthy that the preparations formulated into granules, beads or tablets in which one particle contains both of the rapid-release portion and the slow-release one are advantageous in that they are not accompanied by segregation in the formulation. On the other hand, the mixed preparations which contain the rapid-release component and the slow-release one as separate particles have another merit in that both components can be mixed at an optional ratio.

Experiment 1

(1) Influence of addition of hydrophilic additives on the pinacidil release-rate (i) D-mannitol was added into a hydrophilic additive as an excipient in order to make three kinds of practically insoluble slow-release plain granules A, B and C as shown below, each of which was made by the wet granulation method. Then, the pinacidil release-rate on each granule aforementioned was investigated (FIG. 7). In those preparations, methylcellulose was adopted as a binder, of which the relative amount to D-mannitol was changed as follows.

TABLE 1

| | Ingredient of plain granules (% w/w) | | |
|---|---|---|---|
| | A | B | C |
| pinacidil | 22.5 | 22.5 | 22.5 |
| D-mannitol | 76.25 | 75.0 | 72.5 |
| Methylcellulose (25 cps) | 1.25 | 2.5 | 5.0 |
| total | 100 | 100 | 100 |

The dissolved percent of pinacidil was measured according to the second method (the paddle method) for measuring the release-rate, which is defined in Pharmacopoeia of Japan the 10th. edition (hereinafter referred to as J.P. X) at a stirring rate of 100 r.p.m. in an apparatus as defined therein. As the test medium, 900 ml of the second fluid used in the disintegration test as defined in J.P. X was employed. This method was applied to all of the tests for release-rate in the following experiments.

(ii) D-mannitol was employed as a hydrophilic additive in various relative-ratios to a hydrophilic additive (magnesium stearate). The resulting plain slow-release granules D, E and F of a nondisintegration type having the component as shown in Table 2, which were prepared by the wet granulation method, were employed, in order to investigate the respective release-rates (FIG. 8). Additionally, a certain amount of methylcellulose was employed as a binder in this experiment.

TABLE 2

| Ingredient of plain granules (% w/w) | | | |
|---|---|---|---|
| | D | E | F |
| pinacidil | 10 | 10 | 10 |
| D-mannitol | 87 | 72 | 57 |
| magnesium stearate | 0 | 15 | 30 |
| methylcellulose (25 cps) | 3 | 3 | 3 |
| total | 100 | 100 | 100 |

(iii) D-mannitol as a hydrophilic additive and both of magnesium stearate and hydrogenated castor oil as retarding agents were employed in their various amounts as illustrated below. In order to investigate the pinacidil release-rate, the slow-release beads G, H and I were prepared by layering the respective component as shown below on the surface of the 24–42 mesh spherical beads of sucrose [trade name; Nonpareil®, (Freund Ind. Co. Ltd.)] by a coating method (FIG. 9).

TABLE 3

| Ingredient of slow-release beads (% w/w) | | | |
|---|---|---|---|
| | G | H | I |
| Non-pareil ® | 35.6 | 35.6 | 35.6 |
| pinacidil | 15.4 | 15.4 | 15.4 |
| D-mannitol | 36.7 | 33.3 | 33.5 |
| hydrogenated castor oil | 4.0 | 8.3 | 15.2 |
| magnesium stearate | 8.0 | 7.1 | 0 |
| methylcellulose (25 cps) | 0.3 | 0.3 | 0.3 |
| total | 100 | 100 | 100 |

(iv) In addition to lactose, crystalline cellulose and/or talc were employed as hydrophilic additives in order to make practically insoluble slow-release plain granules, J, K, L, M, N and O by the wet granulation method at the following respective ratios of hydroxypropylcellulose (HPC) paste to methylcellulose (MC) paste by weight. Then, the release-rate in each of those granules was investigated (FIG. 10).

TABLE 4

| Ingredient of slow-release plain granules (% w/w) | | | | | | |
|---|---|---|---|---|---|---|
| | J | K | L | M | N | O |
| pinacidil | 22.5 | 22.5 | 22.5 | 22.5 | 22.5 | 22.5 |
| lactose | 53.75 | 53.75 | 53.75 | 47.5 | 47.5 | 47.5 |
| crystalline cellulose | 18.75 | 18.75 | 18.75 | — | — | — |
| talc | — | — | — | 25 | 25 | 25 |
| hydroxypropylcellulose (HPC) | 3.75 | 2.5 | 1.25 | 2.5 | 1.25 | — |
| methylcellulose (MC) 25 cps | 1.25 | 2.5 | 3.75 | 2.5 | 3.75 | 5 |
| total | 100 | 100 | 100 | 100 | 100 | 100 |
| Ratio as HPC/MC (by weight) | 75/25 | 50/50 | 25/75 | 50/50 | 25/75 | 0/100 |

(v) The slow-release beads P', Q' and R' were made by coating the surface of the slow-release beads having the component mentioned below which were prepared in the same way as in (iii) with an enteric coating material and/or water-insoluble coating material as shown in Table 6. The change of the release-rate on those beads was investigated in connection with the change of water-insoluble materials shown in Table 6 (FIG. 11).

TABLE 5

| Ingredient of slow-release beads (% w/w) | |
|---|---|
| Non-pareil ® | 41.5 |
| pinacidil | 18.0 |
| D-mannitol | 15.9 |
| stearic acid | 2.08 |
| methylcellulose 25 cps | 0.15 |
| total | 77.63 |

TABLE 6

| Ingredient of water-insoluble materials | | | |
|---|---|---|---|
| | P | Q | R |
| Eudragit ® E 30D | 0 | 25 | 40 |
| Eudragit ® L 30D | 100 | 75 | 60 |

The slow-release beads prepared according to Table 5 were coated with the water-insoluble material P, Q and R shown in Table 6 to give the slow-release beads P', Q' and R' respectively.

(2) Results and Discussion

As mentioned above, the change in release-rate of the preparations caused by the additives was examined on various kinds of granules and beads. As the result, it was found that the release-rate in the second fluid (J.P. X, pH 6.8), an simulated intestinal fluid, was controlled by means of adding a hydrophilic additive alone or as a mixture with a retarding agent to pinacidil. It was also found that the addition of suitable amount of preferred binders or the further coating with the water-insoluble material as shown in (v) delayed the release-rate.

Experiment 2

(1) The examination of the release-rate in the first or second fluid (as defined in the disintegration test in J.P. X) on the slow-release granules or beads covered with an enteric coating-film or a water-insoluble film.

(a) component of enteric coating films

The enteric coating solution which had beforehand been prepared as shown in the accompanying table was employed to form the corresponding enteric coating film by means of the spray coating method.

TABLE 7

| Ingredient of enteric coating solution (% w/w) | |
|---|---|
| Eudragit ® L | 5.8 |
| white shellac | 0.65 |
| glycerin fatty acid ester | 2.2 |
| talc | 5.4 |
| ethanol | 85.95 |
| total | 100 |

Figure 12:
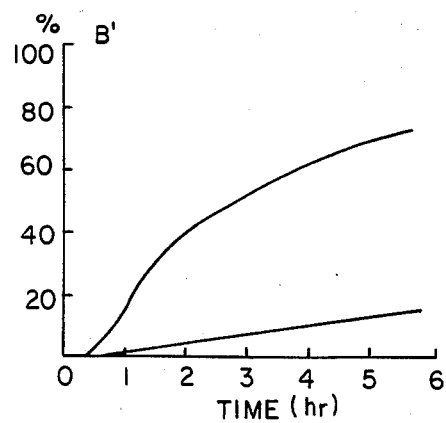

(i) The release-rate in the first or second fluid was examined on the slow-release granules B', which were made by spray-coating the granules B prepared in Experiment (2-i) with the enteric coating solution aforementioned in a pear-type sugar-coating pan (FIG. 12). The coating solution was applied so as to be in an amount (after dried) of 50% of the plain granules B by weight.

Figure 13:
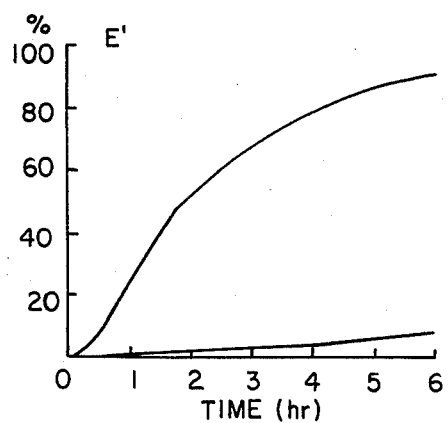

(ii) The slow-release granules E' were prepared by enteric-coating the granules E prepared in Experiment (1-ii) in the same manner as in Experiment (2-i), and the dissolution thereof was examined (FIG. 13).

Figure 14:
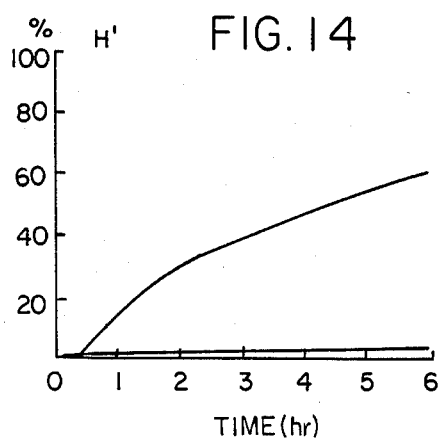

(iii) The slow-release granules H' were prepared by enteric-coating the beads H made in Experiment (1-ii) in the same manner as in Experiment (2-i), and the dissolution-rate thereof was examined (FIG. 14).

(iv) In the same manner as described above, the dissolution-rates were examined on the slow-release beads P', Q' and R', respectively (Table 8 and FIG. 11).

TABLE 8

| | Dissolution-rate in the first fluid | | |
|---|---|---|---|
| | P' | Q' | R' |
| E 30D/L 30D | 0/100 | 25/75 | 40/60 |
| dissolved percent after 4 hours (%) | 4.2 | 8.1 | 13.5 |

(2) Results and Discussion

From those findings, it was clear that the slow-release component coated with enteric coating film show much lower dissolution in the first fluid (around pH 1.2), and the release-starting time in the second fluid is delayed by 0.5 hour behind that of the slow-release component with no enteric coating, but no change is observed in the subsequent dissolution-rate (B', E' and H'). Moreover, the dissolution-rate in the components (P', Q' and R') coated with water-insoluble materials showed low values in the first fluid (Table 8), and the desired values in the second fluid without delay of the release (FIG. 11).

Therefore, it was found that the components which have such desired release-rates in the intestinal juice but no release in the gastric juice (acidic) could be prepared by means of coating with an enteric coating film or a water-insoluble one.

Experiment 3

1. Dissolution-rate of the rapid-release portion in the first or second fluid which was coated on the surface of the slow-release component, and the influence on the dissolution-rate of the slow-release portion covered by the rapid-release portion.

TABLE 9

| Ingredient of the rapid-release layer coating solution (% w/w) | |
|---|---|
| pinacidil | 1.3 |
| lactose | 11.3 |
| macrogoal 6000 | 0.5 |
| hydroxypropylcellulose | 1.4 |
| purified water | 85.5 |
| total | 100 |

Figure 15:
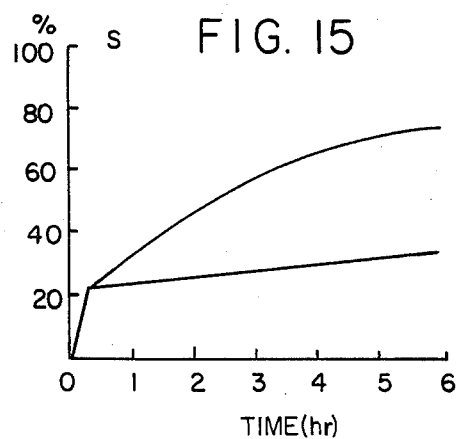

(i) The slow-release granules B' prepared in Experiment (2-i) was coated with the coating solution indicated above to form a rapid-release layer by a fluidizing-bed coating method, in order to make multi-layer granules, namely the sustained-release preparations S'; the dissolution-rate in the first or the second fluid was investigated (FIG. 15).

The coating solution to form the rapid-release layer was enployed in an amount of 42% (after dried) of the slow-release granules B' by weight; the ratio of pinacidil in the rapid-release portion to that in the slow-release one is 2:8 by weight.

(2) Results and Discussion

In such multi-layer preparations, 20% (the total amount of pinacidil in the rapid-release portion) of the total amount of pinacidil in the preparations was released in both of the first and second fluids within a period of the first 15 minutes. Then, the pinacidil was gradually released in the second fluid over a long period of time, but no release was observed in the first fluid. In other words, it was confirmed that the rapid-release portion release pinacidil rapidly at any pH-range (acidic-alkaline), and on the other hand, the slow-releases portion hardly release around the acidic range, but it gradually releases the around neutral range over a long period of time.

Finally, it was found that multi-layer preparations made by coating the slow-release component with rapid-release layers satisfied the condition required for the present sustained-release preparations.

Experiment 4

As described in the Description of the Preferred Embodiments, the actual values of blood-level on the bases of which the optimum combination-ratios were determined and the methods for estimating the expected blood-level from the actual values are explained in more detail as follows: (FIG. 3).

(i) Actual blood-level on the administration of rapid-release component (the base for illustrating the curve of the 10:0 preparations as shown in FIG. 3).

The rapid-release components prepared in Example 7 were administered (at a dose of 10 mg as pinacidil) to four healthy volunteers 30 minutes after usual meals. Then, 5 ml of the blood samples were collected from them at every time as shown in Table 10 (the total number of the sampling amounts to 9 after the administration) in order to measure the blood-levels of pinacidil by HPLC.

TABLE 10

| Blood-levels (ng/ml) after the administration of rapid-release granules (at a dose of 10 mg as pinacidil) | | | | | | | | | |
|---|---|---|---|---|---|---|---|---|---|
| | time (hrs) | | | | | | | | |
| volunteers | 0.5 | 1 | 2 | 3 | 4 | 5 | 7 | 10 | 24 |
| A | 4.1 | 30.3 | 61.9 | 48.8 | 35.0 | 26.5 | 11.3 | 5.4 | 1.8 |
| B | 6.9 | 35.2 | 60.6 | 49.6 | 39.2 | 28.6 | 13.6 | 6.1 | 0.0 |
| C | 3.3 | 13.8 | 58.7 | 75.4 | 58.6 | 48.0 | 25.7 | 12.9 | 1.6 |
| D | 0.0 | 8.7 | 70.3 | 53.5 | 41.6 | 34.1 | 17.7 | 10.5 | 0.0 |
| average | 3.6 | 22.0 | 62.9 | 56.8 | 43.6 | 34.3 | 17.1 | 8.7 | 0.9 |

In Table 10, the actual blood-levels of pinacidil in the prefixed hours on 4 persons of the volunteers are shown by the average value over time. The blood-level curve of the 10:0 preparations in FIG. 3 is derived by plotting the points of the average values.

(ii) Actual blood-levels on the administration of slow-release preparations [the base for illustrating the 0:10 curve in FIG. 3].

The slow-release granules E' prepared in Example 6 were administered (at a dose of 10 mg as pinacidil) to three persons of the same four volunteers as in Experiment (4-i), and then the pinacidil blood-levels of them were analysed over time in the same manner as in the steps shown in (i) (Table 11).

The average blood-level of three persons at hourly intervals is also shown in Table 11, which is depicted as a graph of the 0:10 preparations in FIG. 3.

TABLE 11

Blood-level (ng/ml) after the administration of slow-release granules E' (10 mg as pinacidil)

| volunteer | time (hrs) | | | | | | | | | | |
|---|---|---|---|---|---|---|---|---|---|---|---|
| | 1 | 2 | 3 | 4 | 5 | 6 | 7 | 8 | 10 | 12 | 24 |
| A | 0.0 | 0.0 | 2.1 | 3.0 | 6.4 | 11.0 | 15.7 | 21.5 | 21.7 | 24.6 | 1.7 |
| B | 0.0 | 0.0 | 2.5 | 3.3 | 9.0 | 9.2 | 17.3 | 22.5 | 21.2 | 19.3 | 6.6 |
| C | 0.0 | 0.0 | 0.0 | 2.4 | 5.6 | 9.5 | 12.3 | 13.4 | 16.5 | 19.8 | 5.9 |
| average | 0.0 | 0.0 | 1.5 | 2.9 | 7.0 | 9.9 | 15.1 | 19.1 | 19.8 | 21.2 | 4.7 |

(iii) Blood-level curves expected after the administration of a mixture of the rapid-release granules and the slow-release granules at various prefixed combination-ratios. [the manner of deriving the (8:2–1:9) curves as shown in FIG. 3]

The values in Experiments (i) and (ii) mean the blood-level after administration of the rapid-release components or of the slow-release ones. The blood-level curves represented by the ratios 8:2–1:9 were derived by means of proportional calculation on the assumption that the blood-levels of pinacidil when the preparation consisting of rapid-release components and slow-release ones, which had been mixed at a certain prefixed combination-ratio, were administered in the same manner as described in Experiments (i) and (ii) correspond to the sum of the respective blood-level curves of the two basic 0:10 and 10:0 preparations mentioned above.

Experiment 5

1. Blood-level on the multi-layer granules

In case of the preparations different from those of Experiment 4 in which the slow-release portion is covered with the rapid-release layer, it is presumed that the release-rate in the former portion will be influenced by the latter. From this viewpoint, the multi-layer granules S prepared in Example 10 [the same as that of Experiment 3-i)] was administered (at a dose of 10 mg as pinacidil) to four healthy volunteers in the same manner as in Experiment 4 in order to determine the blood-levels (FIG. 16). Accordingly, for comparison with those findings, both of the blood-level curves for administration of the rapid-release granules as described in Example 7 and for the slow-release granules B' in Example 6 (the granules B' correspond to the slow-release portion of the multi-layer granules) were drawn on the same graph (FIG. 16).

(Results)

The blood-level curve after the administration of the multi-layer granules employed above (the ratio of the pinacidil of the rapid-release portion to that of the slow-release one is 2:8 by weight) was very similar to that (drawn as a dotted line in the same manner as in Experiment 4) which was expected on the administration of a mixture of the rapid-release granules and the slow-release granules at a ratio of 2:8.

From the above point of view, it was found that the optimum combination-ratio of the respective component in the multi-layer preparations was also reasonably given in the same manner as in Experiment (4) in the Detailed Description.

Experiment 6

1. Change of Mean Blood Pressure (ΔMBP) influenced by the rapid-release preparations or the sustained-release preparations All of the clinical tests and estimation thereof described in this application were carried out according to "Guideline for the appreciation of hypotensors" [Iyakuhin Kenkyu 10 (4), 849–864 (1979)].

Figure 1:
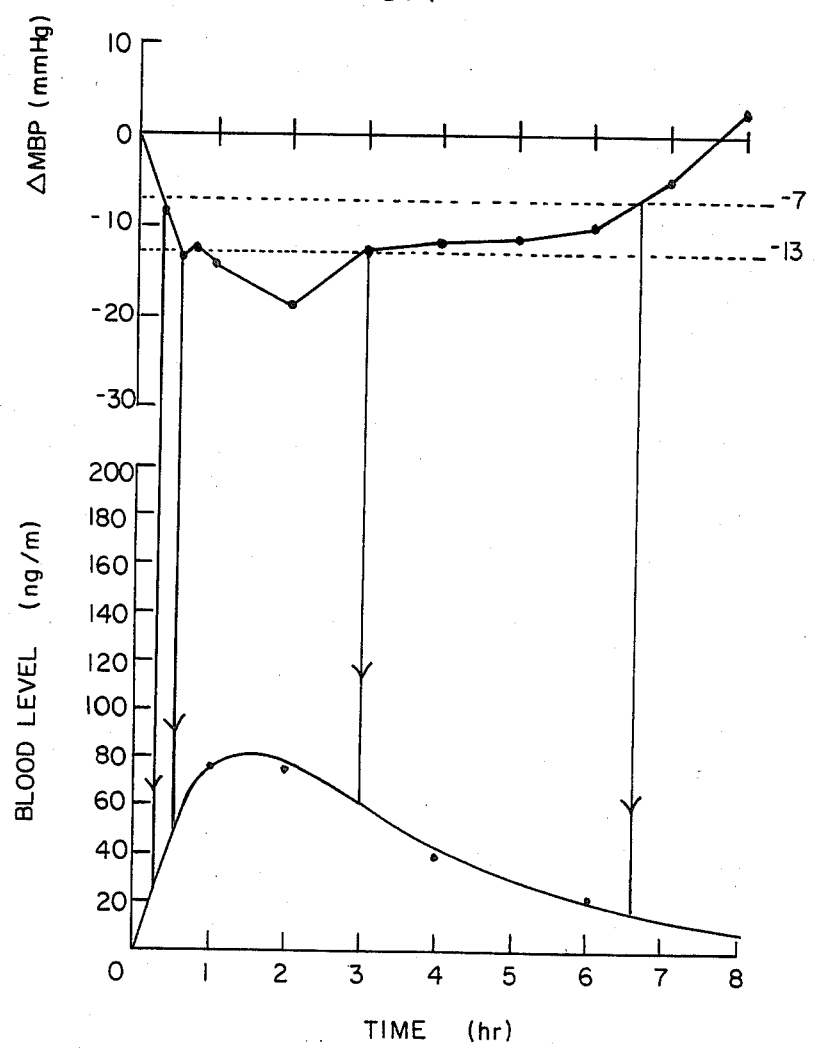
FIG. 1 shows the relationship between the blood-level of pinacidil and the degree of antihypertension (ΔMBP), which is drawn by the average of five inpatients suffering from hypertension on administration of the rapid-release component (10 mg as pinacidil). The axis of the ordinate shows the blood-level of pinacidil or ΔMBP, and the axis of the abscissa shows time (hr).
Figure 2:
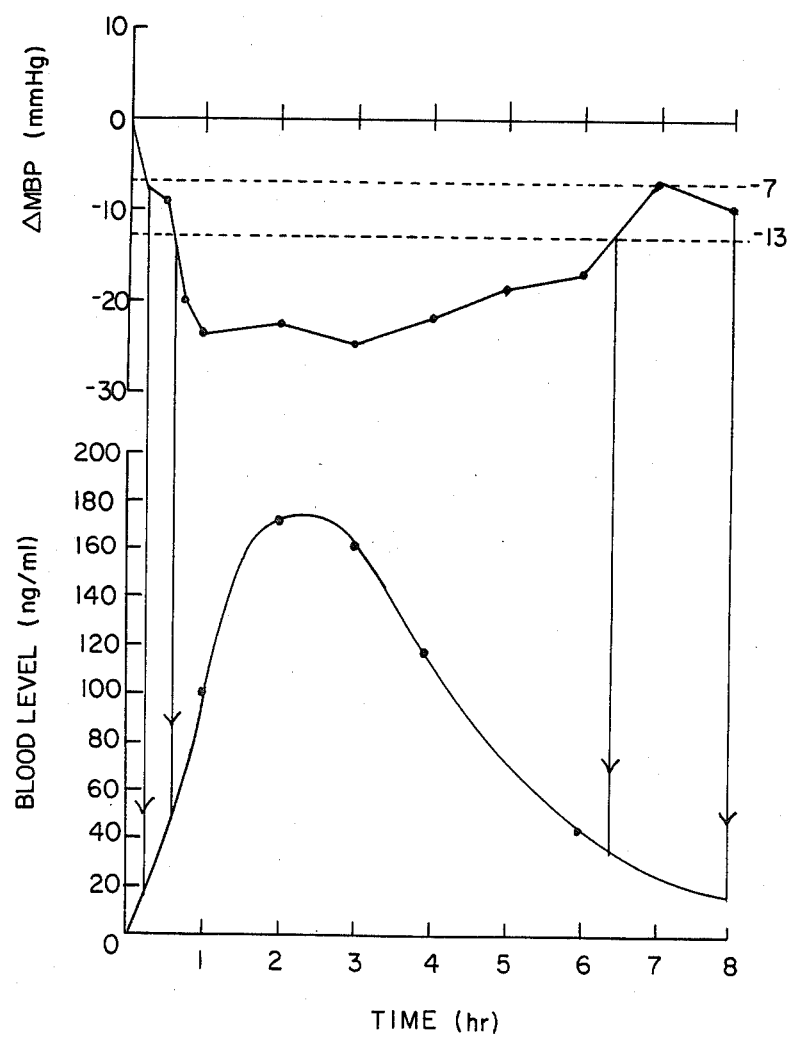
FIG. 2 shows the relationship between the blood-level of pinacidil and the degree of antihypertension (ΔMBP), which is drawn by the average of five inpatients suffering from hypertension on administration of the rapid-release component (20 mg as pinacidil). The ordinate shows the blood-level of pinacidil or ΔMBP and the abscissa shows time (hr).

(i) Effects of the rapid-release preparations on ΔMBP (FIG. 1, FIG. 2).

The rapid-release preparations in Example 7 formulated into capsules were administered to five inpatients suffering from hypertension 30 minutes after usual meals at a dose of 10 mg and 20 mg each (as pinacidil) in order to determine the blood-levels and the values of Mean Blood Pressure hourly (in the figure, the blood-level curves were drawn on the basis of presumption from the actual values of the blood-levels by means of pharmacokinetic analysis.). The term ΔMBP means the difference between the values of Mean Blood Pressure before and after the administration, and FIGS. 1 and 2 show the average of blood-levels or ΔMBP on the five inpatients.

The estimation of the effect was made according to the aforementioned Guideline and then classified as follows: ΔMBP=7–12 mmHg: slightly effective, ΔMBP=13–19 mmHg: effective (in FIGS. 1 and 2, an arrow shows the blood-level when the effect was estimated as "slightly effective" or "effective").

(ii) Effective of sustained-release preparations on ΔMBP (FIG. 6).

The sustained-release capsules were administered to four healthy volunteers 30 minutes after their usual meals, which were prepared to contain 66 mg of the rapid-release granules in Example 7 and 106 mg of the slow-release granules B' in Example 6 in each capsule (rapid-release portion: slow-release one=2:8, total amount of pinacidil per capsule is 20 mg), in order to determine blood-levels and ΔMBP. Moreover, for the purpose of comparison with the values obtained above, the capsules which were prepared alone with the rapid-release component in Example 7 was administered (20 mg each as pinacidil) to the same volunteers under almost the same conditions, and then the actual values of the blood-levels and ΔMBP were illustrated in the figure.

Table 12 shown below shows the actual values (analysed by HPLC) of the respective blood-levels in the four volunteers on the administration of every preparation, and the marks placed at the numbers of the values indicate the level at which the adverse reaction occurred. FIG. 6 shows the average of the blood-levels or ΔMBP (of the four persons) versus time for each preparation.

TABLE 12

Dosage: 20 mg each as pinacidil

| | The rapid-release component in Exp. (6-i) Subjects | | | | | The sustained-release component in Exp. (6-ii) Subjects | | | |
|---|---|---|---|---|---|---|---|---|---|
| Test Preparation Time (hr) | A | B | C | D | Test Preparation Time (hr) | A | B | C | D |
| 0.5 | 0.0 | 2.3 | 0.0 | 0.0 | 1.0 | 8.4 | 4.4 | 0.0 | 12.8 |
| 1.0 | 30.7 | 101.0 | 29.4* | 48.5 | 2.0 | 31.4 | 20.3 | 16.6 | 23.3 |
| 2.0 | 127.0 | 119.7* | 106.4* | 115.7* | 3.0 | 36.5 | 29.7 | 22.8 | 32.9 |
| 3.0 | 120.3 | 141.2* | 123.5* | 141.2* | 4.0 | 31.7 | 29.2 | 30.0 | 34.2 |

TABLE 12-continued

| | Dosage: 20 mg each as pinacidil | | | | | | | | | |
|---|---|---|---|---|---|---|---|---|---|---|
| | The rapid-release component in Exp. (6-i) | | | | | The sustained-release component in Exp. (6-ii) | | | | |
| Test Preparation | Subjects | | | | Test Preparation | Subjects | | | | |
| Time (hr) | A | B | C | D | Time (hr) | A | B | C | D | |
| 4.0 | 98.8 | 112.3* | 98.7* | 116.6* | 5.0 | 35.5 | 37.0 | 56.8 | 32.4 | |
| 5.0 | 70.6 | 77.5* | 65.0 | 88.3* | 6.0 | 41.0 | 64.9 | 87.8* | 60.5 | |
| 7.0 | 31.3 | 38.6* | 26.1 | 40.9* | 7.0 | 81.1 | 92.8 | 66.8* | 78.8 | |
| 10.0 | 12.7 | 15.5 | 8.9 | 19.8 | 8.0 | 85.5 | 91.7 | 45.3 | 78.0 | |
| 24.0 | 2.5 | 2.0 | 0.0 | 0.0 | 10.0 | 40.1 | 52.3 | 22.3 | 53.8 | |
| | | | | | 12.0 | 22.4 | 43.3 | 11.6 | 28.9 | |
| | | | | | 24.0 | 3.8 | 4.9 | 2.3 | 6.3 | |

Note:
The value referred by the asterisk* means the blood-level (ng/ml) at which the subject had a headache.

This invention is explained in more detail according to the following Examples, which are not intended to limit the scope of this invention.

EXAMPLE 1

Preparation of slightly soluble type slow-released plain granules

| Ingredient | (% w/w) |
|---|---|
| pinacidil | 22.5 |
| D-mannitol | 75.0 |
| methylcellulose | 2.5 |
| total | 100 |

To a mixture of 90 g of pinacidil and 300 g of D-mannitol is added 64 g of 16% methylcellulose paste, and the mixture is kneaded by a twin-shell blender and then made into cylindrical granules by a rotary wet granulator of 0.7 m/m bore; the resulting granules are dried at 50° C. for an hour to give the slightly soluble type slow-release plain granules B.

EXAMPLE 2

Preparation of non-disintegration type slow-release plain granules

| Ingredient | (% w/w) |
|---|---|
| pinacidil | 10 |
| D-mannitol | 72 |
| magnesium stearate | 15 |
| methylcellulose 25 cps | 3 |
| total | 100 |

To a mixture of 30 g of pinacidil, 216 g of D-mannitol and 45 g of magnesium stearate is added 56 g of the 16% methylcellulose paste, and the mixture is kneaded with a twin-shell blender and then formulated into the cylindrical non-disintegration type slow-release plain granules E by a rotary wet granulator of 0.7 m/m bore.

EXAMPLE 3

Preparation of practically insoluble slow-release plain granules

| Ingredient | (% w/w) |
|---|---|
| pinacidil | 22.5 |
| lactose | 53.75 |
| crystalline cellulose | 18.75 |
| hydroxypropylcellulose | 2.5 |
| methylcellulose 25 cps | 2.5 |

-continued

| Ingredient | (% w/w) |
|---|---|
| total | 100 |

In the same manner as described in Example 1, the practically insoluble slow-release plain granules K consisting of the above component are made.

EXAMPLE 4

Preparation of slightly soluble type slow-release plain granules

| Ingredient | (% w/w) |
|---|---|
| pinacidil | 22.5 |
| lactose | 47.5 |
| talc | 25.0 |
| hydroxypropylcellulose | 1.25 |
| methylcellulose 25 cps | 3.75 |
| total | 100 |

In the same manner as described in Example 1, slightly soluble slow-release plain granules N of the above component are made.

EXAMPLE 5

Preparation of slow-release plain beads

| Ingredient | (% w/w) |
|---|---|
| Non-pareil ® | 35.6 |
| pinacidil | 15.4 |
| D-mannitol | 33.3 |
| hydrogenated castor oil | 8.3 |
| magnesium stearate | 7.1 |
| methylcellulose 25 cps | 0.3 |
| total | 100 |

Methylcellulose paste (3%) is sprayed at a rate of 7 g/min. to 300 g of 24–42 mesh Non-pareil ® (Freund Ind. Co., LTD.) placed in a centrifugal fluidizing granulator under rotation, during which operation a mixture (540 g as a total amount) of pinacidil, D-mannitol, hydrogenated castor oil and magnesium stearate, which are in the above mixing-ratio, is sprayed for granulation at a rate of about 50 g/min.

After termination of the granulation, the granules are dried by a tray dryer oven to give the slow-release plain beads H.

EXAMPLE 6

Preparation of enteric coating slow-release granules or beads

| Ingredient | (% w/w) |
|---|---|
| Eudragit ® L | 5.8 |
| white shellac | 0.65 |
| glycerin fatty acid ester | 2.2 |
| talc | 5.4 |
| ethanol | 85.95 |
| total | 100 |

An enteric coating solution is prepared according to the above component.

In a pear-form coating pan of 300 mm diameter are placed 600 g of slow-release granules or beads prepared in one of Examples 1 to 5, to which the enteric coating solution is sprayed by an automatic spraying apparatus followed by drying steps under aeration. These steps are repeated until the coating layer reaches 50% of the plain granules or beads by weight. Thus, the enteric coated slow-release preparations B', E', K', N', and H' are prepared.

The following table shows the pinacidil content per 1 g of the enteric coated preparations by weight.

| | preparations | | | | |
|---|---|---|---|---|---|
| | B' | E' | K' | N' | H' |
| pinacidil content (mg) per 1 g of each preparation | 150 mg | 66.7 mg | 150 mg | 150 mg | 103 mg |

EXAMPLE 7

Preparation of rapid-release granules

| Ingredient | (% w/w) |
|---|---|
| pinacidil | 6 |
| lactose | 46 |
| corn starch | 46 |
| hydroxypropylcellulose | 2 |
| total | 100 |

To a powdery mixture (296 g) of pinacidil, lactose and corn starch which is in the above mixing ratio is added 60 g of 10% hydroxypropylcellulose paste and the mixture is kneaded by a twin-shell blender and then formulated into cylindrical granules by a rotary wet granulator, which are dried at 50° C. for an hour by a tray dryer oven and sifted to give 20-40 mesh particles.

One g of the granules contains 60 mg of pinacidil.

EXAMPLE 8

| Ingredient | (% w/w) |
|---|---|
| Non-pareil ® | 23.7 |
| pinacidil | 10.3 |
| sucrose | 33.4 |
| lactose | 30.3 |
| hydroxypropylcellulose | 2.3 |
| total | 100 |

A mixture (935 g) of pinacidil, sucrose and lactose is prepared according to the above component. On the other hand, 3% hydroxypropylcellulose is sprayed to 300 g of 24-42 mesh Non-pareil placed in a centrifugal fluidizing granulator under rotation at a rate of 7 g/min., during which operation the above mixture is sprayed for granulation at a rate of 56 g/min.

After termination of the granulation, the resulting beads are dried at 50° C. for an hour with a tray dryer oven.

The prepared beads contain 103 mg/g of pinacidil.

EXAMPLE 9

Preparation of coating solution as a rapid-release portion for multi-layer granules or beads

| Ingredient | (% w/w) |
|---|---|
| pinacidil | 1.3 |
| lactose | 11.3 |
| macrogoal 6000 | 0.5 |
| hydroxypropylcellulose | 1.4 |
| purified water | 85.5 |
| total | 100 |

According to the mixing-ratio described in the table, macrogoal 6000 and hydroxypropylcellulose are dissolved into purified water, and then a mixture of pinacidil and lactose is added thereto and stirred well to give a coating solution.

EXAMPLE 10

Preparation of multi-layer granules

The slow-release granules B' (400 g) prepared in Example 6 are placed in a fluidizing-bed coating machine (Uniglatt ®) and then coated by spraying 1160 g of the coating solution (as a rapid-release portion) prepared in Example 9 to give multi-layer granules S coated with a rapid-release layer. The dried rapid-release layer is adjusted so as to be 42% of the slow-release granules by weight.

The ratio of pinacidil in the rapid-release portion to that in the slow-release portion is 2:8 by weight, and the resulting multi-layer granules contain 132 mg/g of pinacidil.

EXAMPLE 11

Preparation of the multi-layer beads

By coating 400 g of the slow-release beads H' prepared in Example 6 with 643 g of the coating solution prepared in Example 9 according to the steps as described in Example 10, the multi-layer beads are prepared. In the coating steps, the rapid-release layer to be coated are adjusted at 23% of the slow-release beads by weight in dry state. The resulting multi-layer beads contain 100 mg/g of pinacidil, and the ratio of pinacidil in the rapid-release portion to that in the slow-release portion is 2:8 by weight.

EXAMPLE 12

Preparation of capsules—case 1

The rapid-release granules 7 prepared in Example 7 and the slow-release granules B' or E' in Example 6 are put into capsules according to the following prescription. The numbers shown in the prescription indicate the weight of the respective granules.

(1) Capsule containing 25 mg of pinacidil:
One capsule consisting of

| rapid-release granules 7 | 83 mg |
|---|---|
| slow-release granules B' | 133 mg |

(rapid-release portion: slow-release portion = 2:8 (by the weight of pinacidil))

(2) Capsule containing 12.5 mg of pinacidil:
One capsule consisting of

| | |
|---|---|
| rapid-release granules 7 | 104 mg |
| slow-release granules E' | 94 mg |

(rapid-release portion: slow-release portion = 2:8 (the same as defined above))

EXAMPLE 13

Preparation of capsules—case 2

The rapid-release beads 8 prepared in Example 8 and the slow-release beads H' prepared in Example 6 are placed in capsules at a ratio as shown in the following prescription in order to prepare the capsules containing 25 mg of pinacidil per capsule.

(1) One capsule consisting of

| | |
|---|---|
| rapid-release beads 8 | 49 mg |
| slow-release beads H' | 195 mg |

(rapid-release portion: slow-release portion = 2:8 (the same as defined above))

(2) One capsule consisting of

| | |
|---|---|
| rapid-release beads 8 | 122 mg |
| slow-release beads H' | 122 mg |

(rapid-release portion: slow-release portion = 5:5 (the same as defined above))

EXAMPLE 14

Preparation of capsules—case 3

The respective multi-layer granules or beads prepared in Example 10 or 11 are placed in capsules in a predetermined quantity to yield capsules.

EXAMPLE 15

Preparation of tablets

In advance, granules consisting of the following component with no pinacidil are prepared.

| Ingredient | (% w/w) |
|---|---|
| corn starch | 33.0 |
| lactose | 55.0 |
| carboxymethylcellulose | 10.0 |
| hydroxypropylcellulose | 2.0 |
| total | 100 |

To a mixture of corn starch (99 g), lactose (165 g) and carboxymethylcellulose (30 g) is added 60 g of 10% hydroxypropylcellulose, and the mixture is kneaded by a twin-shell blender. The resulting mixture is formulated into particles by a rotary wet granulator, which are dried and screened forcibly to give granules through a 24 mesh screen.

Then, to 145 g of the resulting granules are added and mixed 190 g of the multi-layer granules prepared in Example 10 and 15 g of magnesium stearate as a lubricant. The mixture is compressed by a tablet machine to produce tablets of 9 mm diameter, 350 mg per tablet.

The ratio of pinacidil in the rapid-release portion to that in the slow-release portion of this tablet is 2:8 by weight. The resulting tablets contain 25 mg of pinacidil per tablet.

What is claimed is:

1. A sustained-release preparation of pinacidil which consists essentially of two different components: one is a rapid-release component dissolving rapidly in the stomach and the other is an enteric coated slow-release component containing hydrophilic additives at 40 to 90 wt% and hydrophobic additives at 30 to 2 wt% based on the slow-release component, wherein the ratio of pinacidil in the respective components is in a range of 4:6 to 1:9 by weight.

2. The sustained-release preparation as claimed in claim 1, wherein the hydrophilic additive is lactose, sucrose, glucose, D-mannitol, sorbitol, inositol, dextrin, xylose, starch, or crystalline cellulose, or the mixture thereof.

3. The sustained-release preparation as claimed in claim 1, wherein the hydrophobic additive is magnesium stearate, hydrogenated castor oil or both.

4. The sustained-release preparation as claimed in claim 1, wherein the slow-release component of pinacidil is covered with an enteric coating film soluble at pH 5.0 to 7.0.

5. The sustained-release preparation as claimed in claim 1, wherein the slow-release component of pinacidil is covered with a water-insoluble coating base.

6. The sustained-release preparation as claimed in claim 1, wherein the enteric coating film is composed of an ingredient selected from the group consisting of (a) methyl methacrylate methacrylic acid copolymer, (b) carboxymethylethylcellulose, (c) shellac and (d) hydroxypropylmethylcellulose phthalate, (e) cellulose acetate phthalate, (f) polyvinylacetate phthalate, (g) ethyl acrylate methacrylic acid copolymer, (h) vinylacetate crotonic acid copolymer, (i) methacrylate methacrylic acid methylmethacrylate copolymer.

7. The sustained-release preparation as claimed in claim 1, wherein the rapid-release component of pinacidil is in the form of powder, fine granules, granules, beads, tablets or a portion thereof.

8. The sustained-release preparation as claimed in claim 1, wherein the slow-release component of pinacidil is in the form of fine granules, granules, beads or tablets.

9. The sustained-release preparation as claimed in claim 1, which is formulated by covering the slow-release component with the rapid-release component.

10. The sustained-release preparation as claimed in claim 1, wherein said ratio is in a range of 3:7 to 2:8.

11. The sustained-release preparation according to claim 1 which is in the form of multi-layer tablets.

12. The sustained-release preparation according to claim 1 which is in the form of multi-layer granules.

13. The sustained-release preparation according to claim 1 which is in the form of multi-layer beads.

* * * * *